United States Patent [19]
Brinkerhoff

[11] Patent Number: 5,700,261
[45] Date of Patent: Dec. 23, 1997

[54] BIPOLAR SCISSORS

[75] Inventor: Ronald J. Brinkerhoff, New Richmond, Ohio

[73] Assignee: Ethicon Endo-Surgery, Inc., Cincinnati, Ohio

[21] Appl. No.: 624,237

[22] Filed: Mar. 29, 1996

[51] Int. Cl.$^6$ ............................................. A61B 17/36
[52] U.S. Cl. .................. 606/41; 606/32; 606/50; 606/48; 606/205
[58] Field of Search .................... 606/32, 39, 40, 606/41, 45, 48, 49, 50, 51, 52, 205–207

[56] References Cited

U.S. PATENT DOCUMENTS

| | | |
|---|---|---|
| 1,659,112 | 2/1928 | Littlejohn . |
| 3,651,811 | 3/1972 | Hildebrandt et al. ............ 128/303.17 |
| 4,092,986 | 6/1978 | Schneiderman ............... 128/303.14 |
| 4,674,498 | 6/1987 | Stasz ............................. 606/48 |
| 4,969,885 | 11/1990 | Farin ............................. 606/38 |
| 5,122,137 | 6/1992 | Lennox ......................... 606/40 |
| 5,290,287 | 3/1994 | Boebel et al. ................. 606/51 |
| 5,324,289 | 6/1994 | Eggers .......................... 606/48 |
| 5,330,471 | 7/1994 | Eggers .......................... 606/48 |
| 5,342,359 | 8/1994 | Rydell .......................... 606/51 |
| 5,352,222 | 10/1994 | Rydell .......................... 606/37 |
| 5,431,674 | 7/1995 | Basile et al. ................. 606/170 |
| 5,443,463 | 8/1995 | Stern et al. .................. 606/51 |
| 5,456,684 | 10/1995 | Schmidt et al. .............. 606/41 |
| 5,462,546 | 10/1995 | Rydell .......................... 606/51 |
| 5,496,312 | 3/1996 | Klicek ........................... 606/34 |

FOREIGN PATENT DOCUMENTS

| | | |
|---|---|---|
| 0 623 316 A1 | 11/1994 | European Pat. Off. . |
| 2 355 521 | 1/1978 | France . |
| 342619 | 6/1972 | U.S.S.R. . |
| 575-103 | 10/1977 | U.S.S.R. . |
| 624616 | 9/1978 | U.S.S.R. . |
| 854-366 | 8/1981 | U.S.S.R. . |
| 944591 | 7/1982 | U.S.S.R. . |
| WO 94/17741 | 8/1994 | WIPO . |

OTHER PUBLICATIONS

"A New Electrosurgical Coagulating–Cutting Forcepts," Doss et al. vol. 74, No. 3, pp. 449–451, Sep. 1973, Surgery.

*Primary Examiner*—Jennifer Bahr
*Assistant Examiner*—Rosiland Kearney
*Attorney, Agent, or Firm*—Bernard Shay

[57] ABSTRACT

A bipolar electrosurgical scissors adapted to electrically cauterize and desiccate organic tissue prior to cutting the tissue in order to reduce or prevent bleeding. The bipolar electrosurgical scissors include a pair of scissor members attached through an electrically insulating point. Each scissor member includes, at a distal end, a shearing surface with a plurality of electrode regions interspersed between a plurality of insulating regions. The insulator regions are offset such that upon closure of the shearing members, the insulation region of one shearing member opposes a corresponding electrode on the other shearing member.

4 Claims, 6 Drawing Sheets

BIPOLAR SCISSORS

FIELD OF THE INVENTION

The present invention relates to bipolar electrosurgical instruments for cutting tissue and, more particularly, to improved bipolar scissors for use in cutting and cauterizing tissue during surgical procedures.

BACKGROUND OF THE INVENTION

The control of bleeding during surgery accounts for a major portion of the time involved in an operation. In particular, it is advantageous to limit the bleeding that occurs when organic tissue is incised or severed. Hemostatic surgical techniques are known for reducing the bleeding from incised tissue prior to, during, and subsequent to incision. One such technique uses a heating element to transfer heat to the severed tissue to thermally form collagen. Heat transferred from the instrument to the tissue produces a thin collagen film which seals the severed blood vessels and capillaries, thus reducing bleeding. Localized application of heat reduces tissue necrosis or damage that may retard healing.

Electrosurgical techniques that pass a high frequency or radio frequency current through the patient's tissue between two electrodes have been used for both cutting and cauterizing. As electrical current passes through tissue, joulean (ohmic) heating occurs in the tissue causing hemostasis by denaturing tissue proteins to form a coagulum that seals the bleeding sites. The heat generated in the tissue is a function of the current density and the electrical resistance of the tissue.

In bipolar electrosurgical devices, such as bipolar scissors, which may also be referred to as bipolar shears, the electrodes are generally located on the shearing members. In such devices, current flow is substantially confined to the tissue disposed between the electrodes. The tissue acting as a conductor, conducts electricity from one electrode to the other. Bipolar electrosurgical devices such as bipolar scissors are therefore advantageous in that they help to localize current flow within the patient.

Hildebrandt et al. U.S. Pat. No. 3,651,811, U.S. Pat. No. 5,324,289, U.S. Pat. No. 5,330,471 and Soviet Union Patent Certificate 575,103 describe bipolar electrosurgical scissors having opposing cutting blades forming active electrodes. These devices enable a surgeon to sequentially coagulate the blood vessels contained in the tissue and mechanically sever the tissue with the scissor blades.

It would, therefore, be beneficial to provide bipolar electrosurgical scissors wherein electrical current flows between the shearing surfaces and through the tissue that is about to be or is being cut and not directly between the shearing surfaces, thus preventing short circuits between blades.

SUMMARY OF THE INVENTION

The present invention is directed to a bipolar electrosurgical scissors-like instrument wherein each scissor member includes a plurality of electrode regions for causing hemostasis of tissue and a shearing surface on a shearing member for mechanically severing tissue. Non-continuous regions of insulating material are disposed on each of the shearing surfaces of the scissors so that the electrically active portions of the scissor members do not contact each other at any point during operation of the instrument. The shearing surfaces may include both electrode and insulation regions which interleave as the scissor members are closed and the shearing surfaces are brought together.

In one embodiment, an electrosurgical instrument constructed in accordance with the present invention comprises a scissors-like instrument including first and second scissor members. Each scissor member comprises a blade-like portion or shearing member having a shearing surface, a cutting edge and an exterior surface. Each shearing surface includes a plurality of insulation regions separated by electrode regions. The cutting edge and shearing surface are formed from regions of both the electrode and insulation. The first and second scissor members are connected by connecting means so that the respective shearing surfaces move through a range of motion in a conventional scissors-like cutting action. The cutting action defines a cutting point that moves along the cutting edges of the respective shearing members through the range of motion. The instrument further includes a plurality of electrode regions on each shearing member which are connected to a high frequency electrical power supply which is adapted provide a high frequency electrical current to the electrodes when a conductive material such as organic tissue is placed between the shearing members. The electrically insulating material is interposed between the electrodes to prevent the electrodes on the respective shearing members from contacting each other in the range of motion. The insulating material is disposed so that as the scissors are closed and the cutting point advances, the electrodes proximal to the cutting point on one shearing member are alligned with insulation regions on the opposing shearing member to enhance current flow in tissue at and distal to the cutting point.

In a further embodiment of the present invention, the first and second shearing members are made of an electrically conductive material. A first layer of electrically insulating material is disposed on a portion of each of the shearing members, thereby forming electrode regions between the deposited insulation regions, the insulation regions forming a portion of the cutting edge and a portion of the shearing surface of that shearing member.

According to a further embodiment of the present invention, the shearing surfaces of the first and second shearing members have a substantially saw tooth shape. In a further embodiment, the shearing surfaces of the first and second shearing members have a substantially castellated shape.

According to a further embodiment of the present invention, the shearing members include shelf regions.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

3

DETAILED DESCRIPTION OF THE INVENTION

Figure 1:
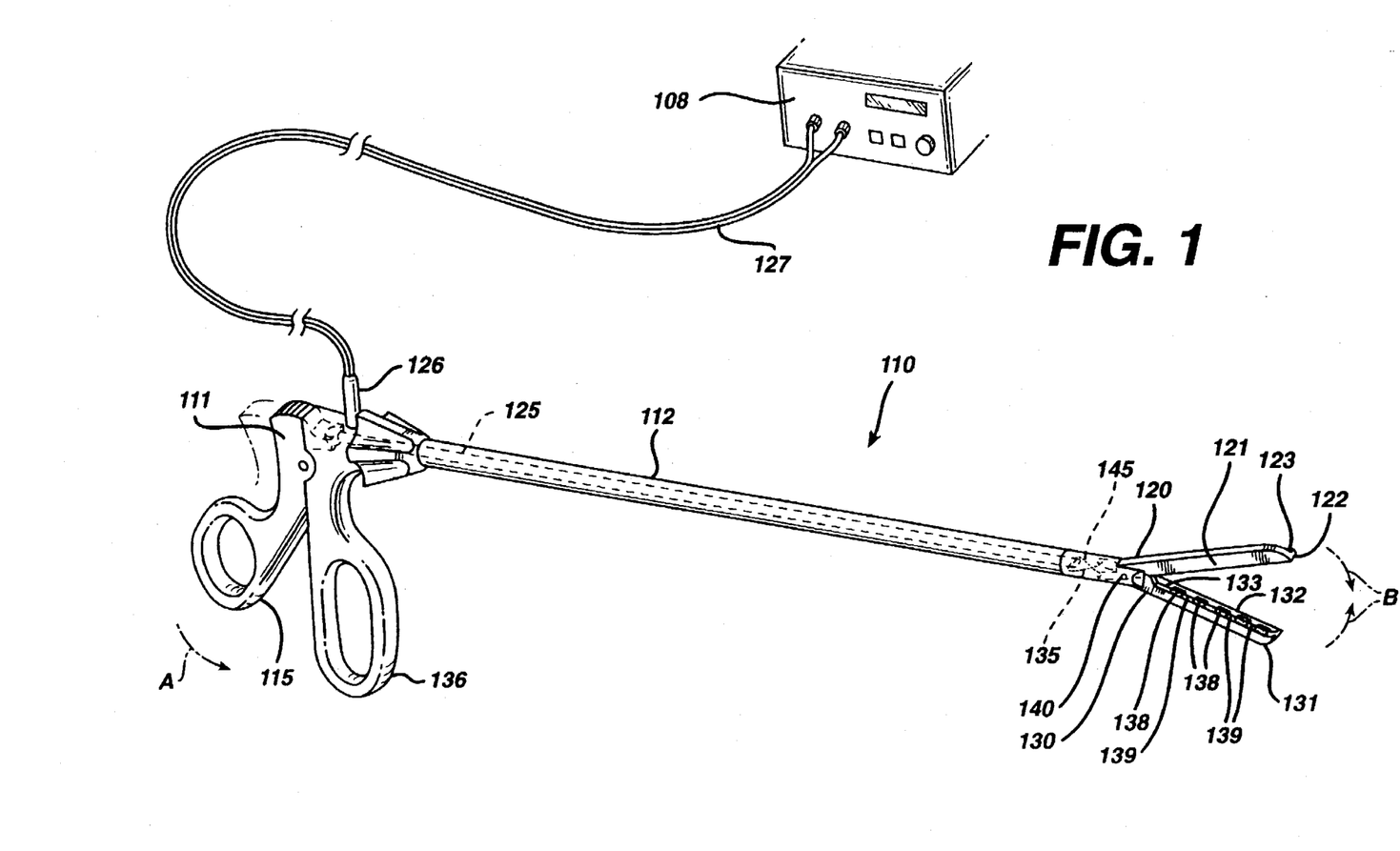
FIG. 1 is a perspective view of bipolar electrosurgical scissors constructed in accordance with one embodiment of the present invention.
Figure 4:
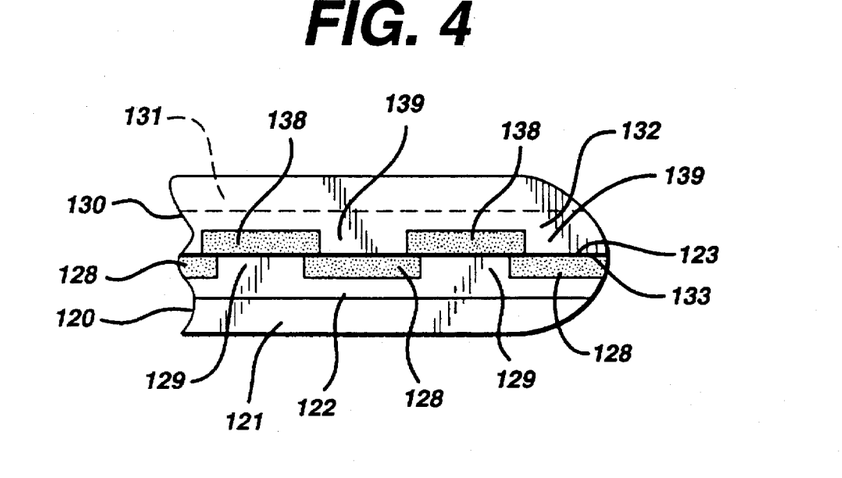
FIG. 4 is a top view of the end effector of the bipolar electrosurgical scissors illustrated in FIG. 3 wherein the shearing members are closed.

FIG. 1 illustrates bipolar electrosurgical scissors 110 for causing hemostasis in and cutting of organic tissue. Scissors 110 includes first scissor member 120 and second scissor member 130 pivotally connected by a fastener 140. Fastener 140 may be, for example, a pivot pin constructed of an electrically insulative material. Scissor member 120 includes shearing member 121 along its distal end. Shearing member 121 includes shearing shelf 122 and cutting edge 123. Shearing shelf 122 includes insulator regions 128 and electrode regions 129 as illustrated in FIG. 4. Cutting edge 123 runs along the length of shelf 122 and may include the edge of insulator regions 128 as well as the edge of electrode regions 129. Scissor member 130 in FIG. 1 includes shearing member 131 along its distal end. Shearing member 131 includes shearing shelf 132 and cutting edge 133. Shearing shelf 132 includes insulator regions 138 and electrode regions 139. Cutting edge 133 runs along the length of shearing member 131 and may include the edge of insulation regions 138 as well as the edge of electrode regions 139 as illustrated in FIG. 4.

In FIG. 1, handle 111 is connected to shearing members 121 and 131 by elongated tube 112 which includes connecting rod 125. Handle 111 includes first grip member 115 and second grip member 136. Connecting rod 125 is attached at its proximal end to grip member 115 and at its distal end to push rod 135 and push rod 145. Push rod 135 connects connecting rod 125 to scissor member 130. Push rod 145 connects connecting rod 125 to scissor member 120. Thus, movement of grip member 115 relative to grip member 136 in direction A results in movement of scissor member 120 relative to scissor member 130 in direction B. While the embodiment of the invention illustrated in FIG. 1 is adapted for use in endoscopic or minimally invasive procedures, the present invention is also adaptable for use with conventional or open bipolar electrosurgical scissors.

Figures 2, 3:
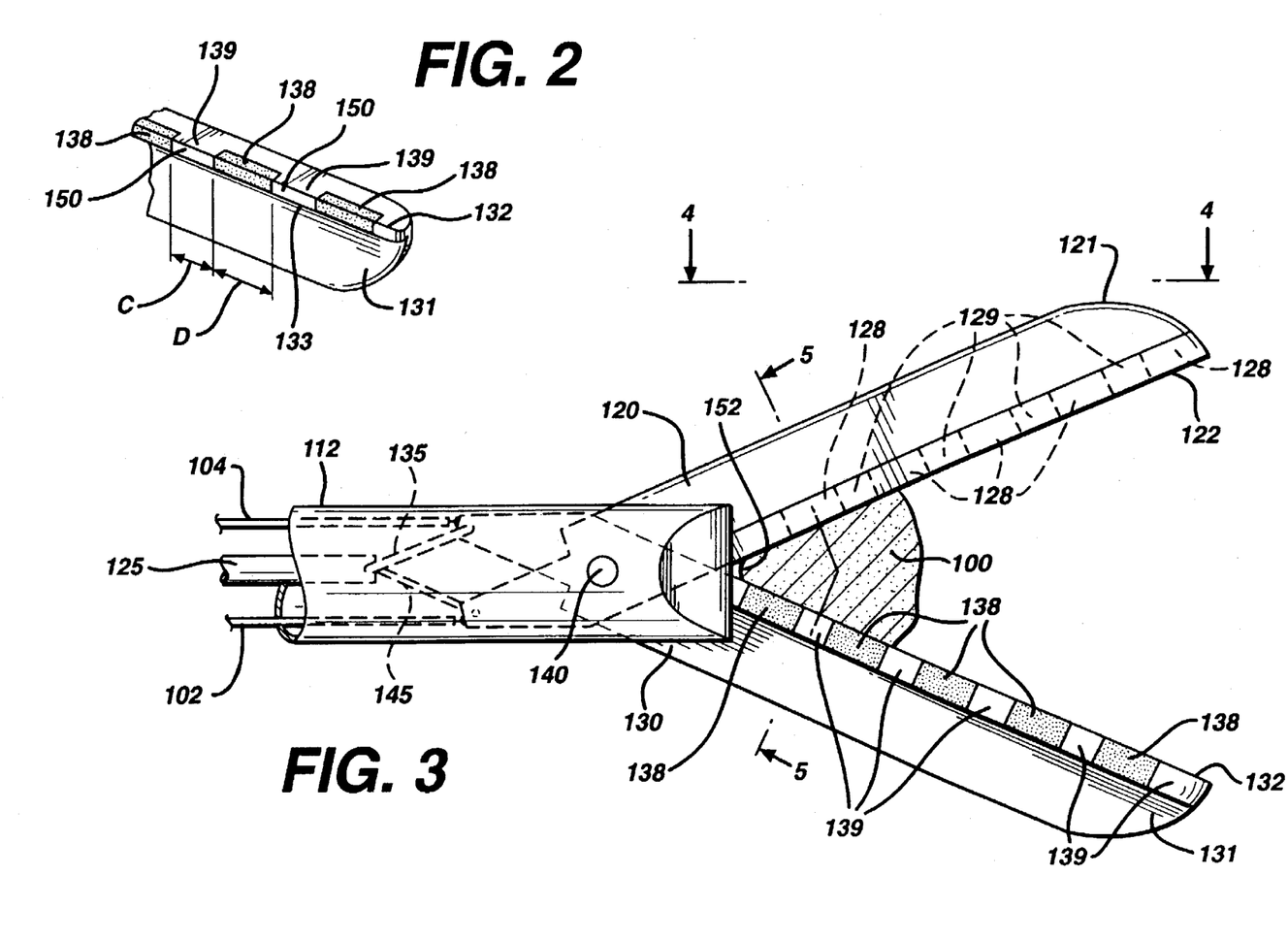
FIG. 2 is a perspective view of the distal end of one shearing member of the bipolar electrosurgical scissors illustrated in FIG. 1.
FIG. 3 is a side view of the distal end of the bipolar electrosurgical scissors illustrated in FIG. 1 whrein tissue is disposed between the shearing members.

Electrical connection 126 connects bipolar scissors 110 to electrical power supply 108 via chord 127. As illustrated in FIG. 3, electrode regions 129 are connected to electrical connection 126 through wire 102 which may be connected to scissor member 120 or, alternatively directly to electrode regions 129. Electrode regions 139 are connected to elec-

4 trical connection 126 through wire 104 which may be connected to scissor member 130 or, alternatively, directly to electrode regions 139.

Power supply 108 may be a high frequency voltage source having a substantially constant voltage at selectable output levels. Such devices are described, for example, in U.S. Pat. Nos. 4,092,986 and 4,969,885. The power supply used in conjunction with the present invention preferably provides an output voltage level that is substantially constant at the user selected level, independent of the electrical resistance encountered by the electrodes. Power may be supplied to the electrode regions of the bipolar scissors by, for example, activating a foot switch. When power is supplied to the electrode regions, for example, regions 129 and 139, current flows through the path of least resistance between the electrode regions, for example, through organic tissue in direct contact with electrode regions 129 and 139.

Electrodes 129 and 139 are preferably made of an electrically conductive, rigid structural material such as stainless steel which is capable of sustaining a sharp cutting edge. Scissor members 120 and 130 may also be made of an electrically conductive, rigid structural material, such as stainless steel. Alternatively, scissor members 120 and 130 may be constructed of electrically insulative material with a wire or other conductor to connect wires 102 and 104 to conductive electrode regions 129 and 139, respectively. Shelf 122 includes insulation regions 128 which separate electrode regions 129. Shelf 132 includes insulation regions 138 which separate electrode regions 139. Insulation regions 128 and 138 are preferably made of an inorganic, electrically insulative, rigid structural material such as glass, ceramic, nitride, boride or synthetic diamond which is capable of sustaining a sharp cutting edge.

Scissor members 120 and 130 are pivotally connected by pivot pin 140 so that cutting edges 123 and 133 move in scissors-like opposition through a range of motion to cut tissue or other material placed between scissor members 120 and 130. Pivot pin 140 may be made of an insulating material, for example, polyamide or nylon. Alternatively, pivot pin 140 may include a combination of non-insulating and insulating materials such as a stainless steel screw insulated by nylon bushings. Scissor members 120 and 130 may include an insulative coating over at least a portion of their surface to electrically insulate the scissor members from each other and from surrounding tissue or other structures. Elongated tube 112 may also include an insulative coating to electrically isolate tube 112. Such insulative coatings may comprise polyvinyl chloride, nylon, plastic or other insulative material and may be applied to other areas of bipolar scissors 110 which are not intended to conduct electricity.

FIG. 2 is a perspective view of the distal end of shearing member 131 of the bipolar electrosurgical scissors 110 illustrated in FIG. 1. Shelf 132 is positioned on shearing member 131. Insulation regions 138 are disposed on shelf 132 to form alternating portions of cutting edge 133. Insulated regions 138 separate electrode regions 139. Electrode regions 139 include face regions 150 which are located on the cutting edge 133 of shelf 132. Insulated regions 138 are separated by a distance C. Electrode regions 139 are separated by a distance D. In one embodiment of the present invention, shorting is prevented by making insulation regions 138 larger than electrode regions 139 (i.e. making distance D larger than distance C) to ensure that insulation regions 138 overlap with insulation regions 128 as scissor members 120 and 130 are closed.

FIG. 3 is a side view of the distal end of the bipolar electrosurgical scissors illustrated in FIG. 1 wherein tissue 100 is disposed between shearing members 121 and 131. The distal intersection of shearing members 121 and 131 forms cutting point 152. Tissue 100 forms an electrically conductive path from electrode regions 129 to electrode regions 139. When an electrical potential is induced between electrode regions 129 and electrode regions 139, current flows through electrically conductive tissue 100, heating the tissue. As tissue 100 is heated, the tissue is desiccated, resulting in coagulation of fluids in the region between shearing members 121 and 131. Once tissue 100 is heated enough to produce hemostasis, scissor members 120 and 130 may be closed to cut or sever the tissue. As shearing members 121 and 131 are closed, cutting edges 123 and 133 are brought together and tissue 100 is cut. Electrosurgical energy may be continuously supplied to tissue 100 as shearing members 121 and 131 are closed since the overlap of insulator regions 128 and 138 will prevent electrode regions 129 and 139 from shorting.

FIG. 4 is a top view of the end effector of the bipolar electrosurgical scissors illustrated in FIG. 3 wherein the shearing members are closed. In FIG. 4, shearing members 121 and 131 are closed and insulators 128 overlap insulators 138 to prevent shorting between electrodes 129 and 139. The overlapping insulation regions 128 and 138 are adapted to cover at least a portion of opposing electrode regions 139 and 129 respectively as the scissor members 120 and 130 are closed. Thus, as shearing members 121 and 131 close, insulation regions 128 and 138 cover opposing electrodes 139 and 129 respectively, cutting off or substantially limiting current flow from the covered portion of the electrode regions. This arrangement enhances current flow between electrodes distal to the cutting point since no potion of those electrodes are covered by the opposing insulation regions, improving current flow and, thus, hemostasis in the uncut tissue. Interspersing insulation regions 128 and 138 between electrode regions 129 and 139 is also advantageous in that it ensures that an active electrode is located at cutting point 152 of shearing members 121 and 131 throughout the entire range of motion.

It will be apparent that the electrical characteristics of the bipolar electrosurgical scissors according to the present invention may be modified by the selective application of an insulative coating to shearing members 121 and 131 and, more particularly, to electrode regions 129 and 139. For example, application of an insulative coating to cover all of shearing member 132 except electrode face 150 may be advantageous. In such a device, electrodes 129 and 139 proximal to cutting point 152 are at least partially turned off by their associated insulation regions 138 and 128 as shearing members 121 and 131 close, turning off or substantially reducing the electrical current through the covered electrode regions.

Figure 5:
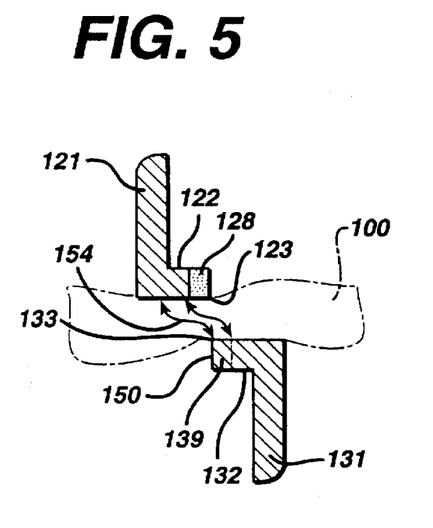
FIG. 5 is a cutaway end view along view 5—5 of the bipolar electrosurgical scissors illustrated in FIG. 3.
Figure 6:
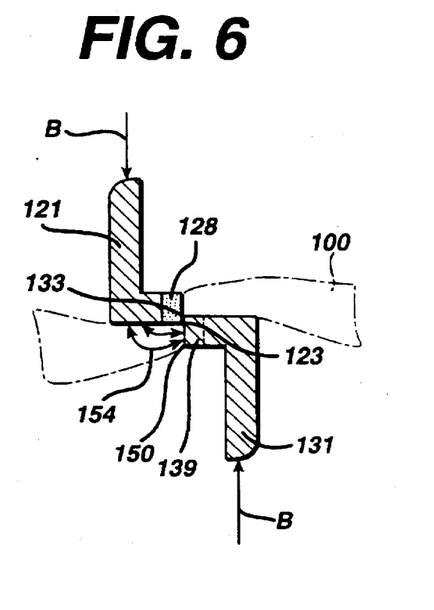
FIG. 6 is a cutaway end view of the bipolar electrosurgical scissors illustrated in FIG. 5 after the end effector is partially closed.

FIG. 5 is a cutaway end view along view 5—5 of shearing members 121 and 131 of the bipolar electrosurgical scissors 110 illustrated in FIG. 3. As shearing members 121 and 131 are closed and electrosurgical energy is applied to scissors 110, electrical current 154 will flow from electrode regions 139, through tissue 100, to electrode regions 129 (not visible in FIG. 5) and to uninsulated portions of shearing member 121 which contact tissue 100. In FIG. 6, shearing members 121 and 131 have been partially closed to cut tissue 100. As shearing members 121 and 131 are closed, electrosurgical energy continues to be applied and electrical current 154 continues to flow through tissue 100 adjacent to electrode regions 139 or electrode regions 129 (not visible in FIG. 6). Tissue 100 is cut by the interaction of cutting edges 123 and 133 as shearing members 121 and 131 move in direction B.

Figure 7:
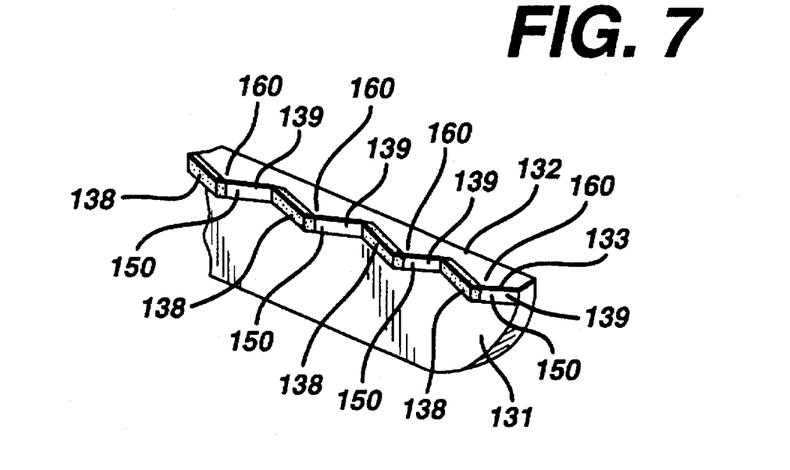
FIG. 7 is a perspective view of the distal end of one shearing member of another embodiment of the bipolar electrosurgical scissors of the present invention.
Figure 8:
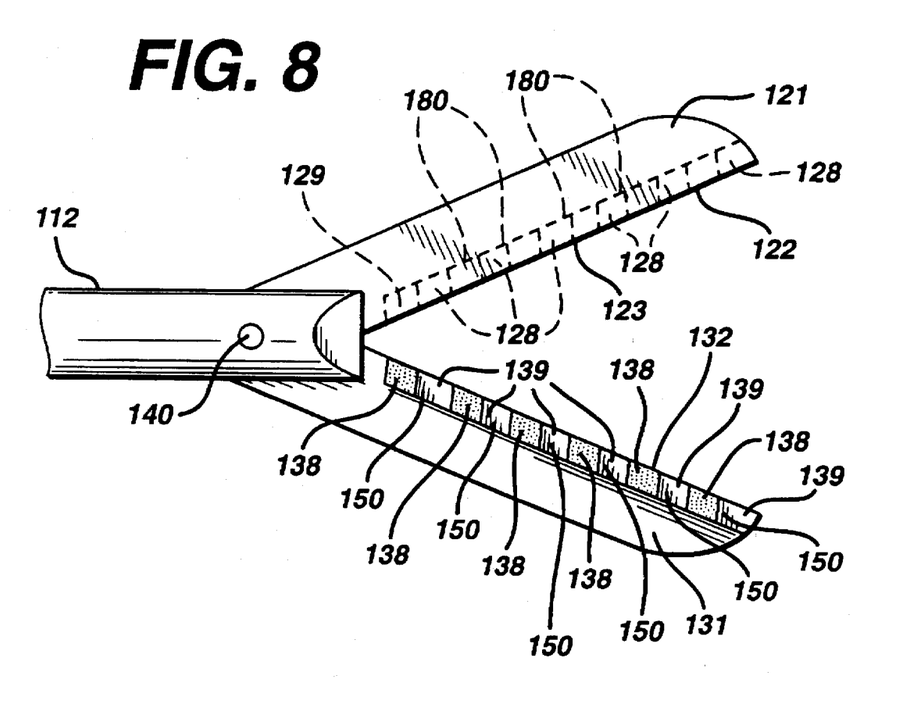
FIG. 8 is a side view of the distal end of the bipolar electrosurgical scissors illustrated in FIG. 7.
Figure 9:
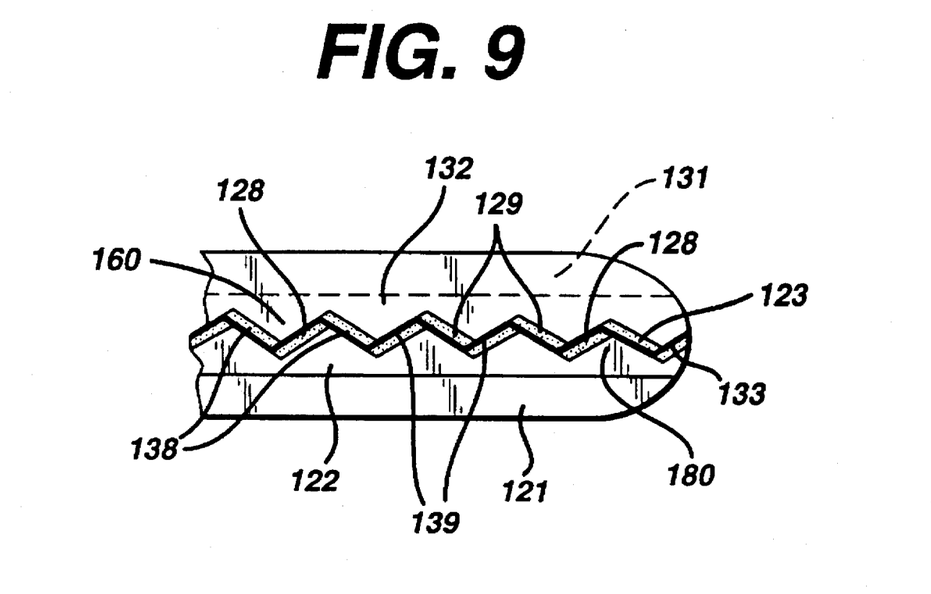
FIG. 9 is a top view of the end effector of the bipolar electrosurgical scissors illustrated in FIG. 8 wherein the shearing members are closed.

FIGS. 7, 8 and 9 illustrate an alternative embodiment of the bipolar electrosurgical scissors illustrated in FIG. 1 and described herein with respect to FIGS. 1–6. Thus, except as modified below, the description heretofore provided with respect to FIGS. 1–6 is applicable to the embodiment of the invention illustrated in FIGS. 7, 8 and 9. In addition, where like reference numbers are used to refer to an element in FIGS. 7, 8 and 9, the description of the element provided with respect to the discussion of FIGS. 1–6 is applicable to the element in FIGS. 7, 8 and 9.

FIG. 7 is a perspective view of the distal end of shearing member 131 in one embodiment of the bipolar electrosurgical scissors 110 of the present invention. In FIG. 7, cutting edge 133 of shelf 132 has a sawtooth shape with insulation regions 138 formed on alternating sides of each sawtooth 160. Electrode regions 139 are interspersed between insulation regions 138 on the side of each sawtooth 160. Electrode regions 139 include face regions 150. FIG. 8 is a side view of one embodiment of shearing members 121 and 131 of bipolar electrosurgical scissors 110 including the sawtooth shelf illustrated in FIG. 7. In FIG. 8, cutting edge 123 of shelf 122 has a saw tooth shape with insulation regions 128 formed on alternating sides of each sawtooth 180. Electrode regions 129 are interspersed between insulation regions 128 on the sides of each sawtooth 180. Electrode regions 129 include face regions 150. FIG. 9 is a top view of the embodiment of the present invention illustrated in FIGS. 7 and 8 wherein shearing members 121 and 131 are closed. The interaction of sawtooth shelf members 160 and 180 is visible in FIG. 9. This embodiment of the present invention may be advantageous because a sawtooth cut may reduce the amount of tearing experienced by the tissue as it is being cut. As illustrated in FIG. 9, in an embodiment of the present invention utilizing a sawtooth shelf, the insulation regions 128 and 138 interleave to prevent shorting. It will be apparent to those of skill in the art that sawtooth shelf members 160 and 180 may also be formed in an arc shape with rounded end points and rounded interior regions between tooth members.

Figure 10:
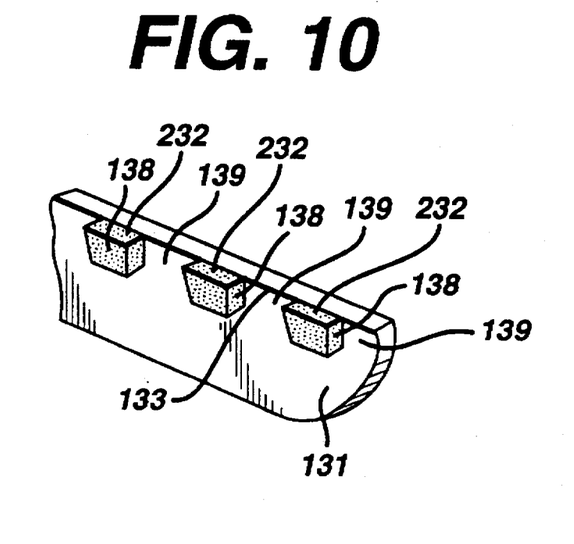
FIG. 10 is a perspective view of the distal end of one shearing member of another embodiment of the bipolar electrosurgical scissors of the present invention.
Figure 11:
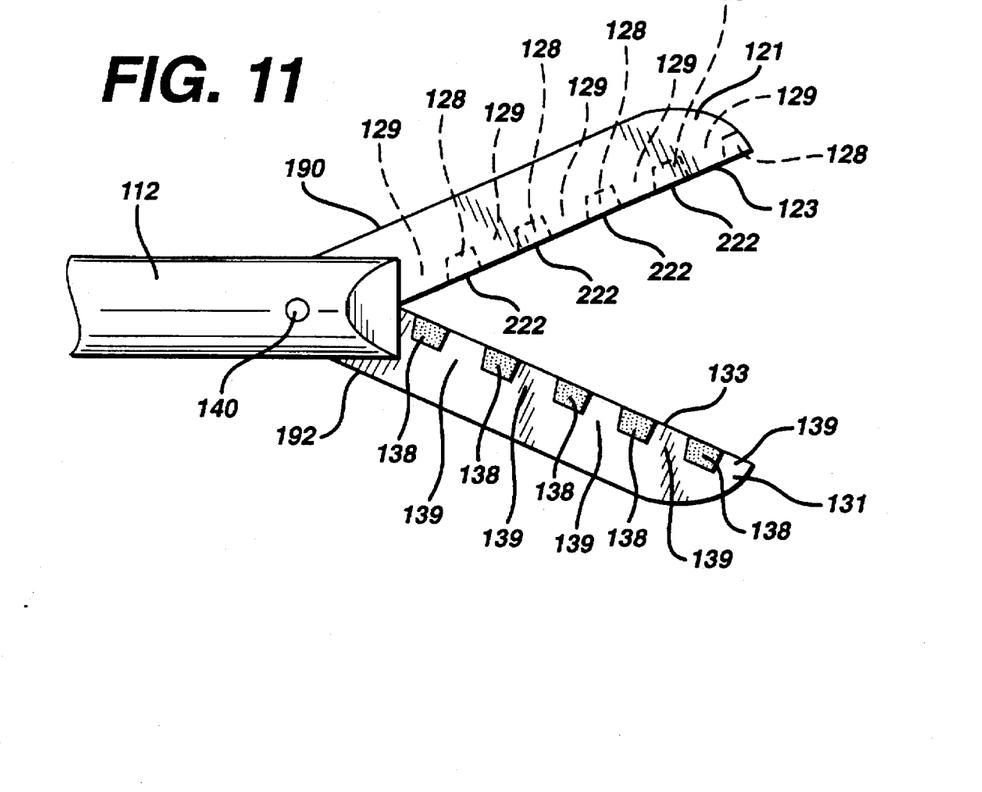
FIG. 11 is a side view of the distal end of the bipolar electrosurgical scissors illustrated in FIG. 10.
Figure 12:
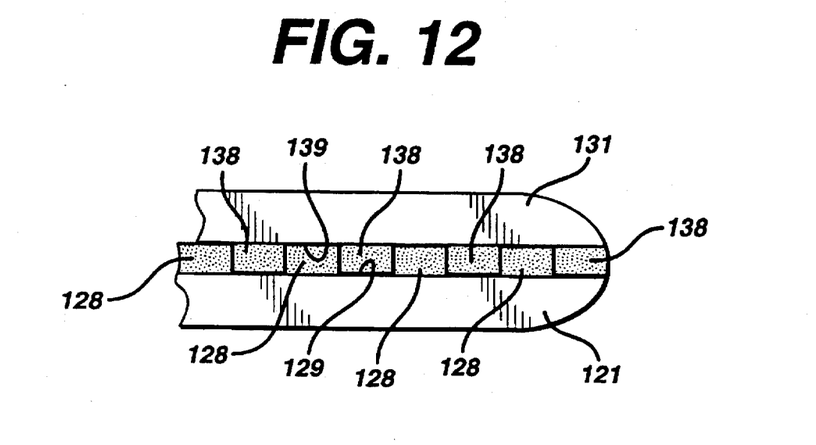
FIG. 12 is a top view of the end effector of the bipolar electrosurgical scissors illustrated in FIG. 11 wherein the shearing members are closed.

FIGS. 10, 11 and 12 illustrate an alternative embodiment of the bipolar electrosurgical scissors illustrated in FIG. 1 and described herein with respect to FIGS. 1–6. Thus, except as modified below, the description heretofore provided with respect to FIGS. 1–6 is applicable to the embodiment of the invention illustrated in FIGS. 10, 11 and 12. In addition, where like reference numbers are used to refer to an element in FIGS. 10, 11 and 12, the description of the element provided with respect to the discussion of FIGS. 1–6 is applicable to the element in FIGS. 10, 11 and 12.

FIG. 10 is a perspective view of the distal end of shearing member 131 in one embodiment of the bipolar electrosurgical scissors 110 of the present invention. In FIG. 10, shelf 232 is discontinuious and comprises a plurality of insulation regions or pilasters 138 formed on shearing member 131. Electrode regions 139 are interspersed on shearing member 131 between insulation regions 138. In FIG. 10, cutting edge 133 extends along the edges of insulation regions 138 and the edges of electrode regions 139. FIG. 11 is a side view of one embodiment of shearing members 121 and 131 of bipolar electrosurgical scissors 110 including a shelf 222 comprising a plurality of insulation regions 128. FIG. 12 is a top view of the embodiment of the present invention illustrated in FIGS. 10 and 11 wherein shearing members 121 and 131 are closed. The interaction of insulation regions 128 and 138 is visible in FIG. 12. This embodiment of the present invention may be advantageous because a castellated cut may reduce the amount of tearing experienced by the tissue as it is being cut. As illustrated in FIG. 12, the insulation regions 128 and 138 interleave to prevent shorting.

It will be apparent that one or more of insulation regions 128 may be extended to cover substantially the full width of shearing member 121 from cutting edge 123 to back edge 190. In this embodiment, electrode regions 129 would be arranged between the extended insulation regions 128. Similarly, it will be apparent that one or more of insulation regions 138 may be extended to cover substantially the full width of shearing member 131 from cutting edge 133 to back edge 192. In this embodiment, electrode regions 139 would be arranged between the extended insulation regions 138. In such an embodiment, insulators 128 and 138 may be curved to facilitate closing of shearing members 131 and 132. In other embodiments of the present invention, coatings of, for example high electrical and thermal conductivity material, e.g., silver or copper, may be applied to the conductive regions of shearing members 121 and 122. Such coatings may also reduce localized heating by dissipating the heat throughout the thermally conducting surface area of the coating. In a bipolar electrosurgical scissors according to the present invention, the insulator regions and electrode regions are arranged such that the electrode regions do not short while providing a high current density through the tissue near the cut.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. An electrosurgical instrument comprising:

a first scissor member including a first shearing member, a first shelf on said first shearing member, a first cutting edge on said first shelf, wherein at least a portion of said first shelf surface includes a plurality of first electrically insulated regions and a plurality of first electrode regions;

a second scissor member pivotally coupled to said first scissor member and including a second shearing member, a second shelf on said second shearing member, a second cutting edge on said second shelf, wherein at least a portion of said second shelf includes a plurality of second electrically insulated regions and a plurality of second electrode regions, said second insulated regions being arranged opposite said second electrode regions.

2. An electrosurgical instrument according to claim 1 wherein said first and second cutting edges overlap when said instrument is closed to form a region of overlap and said first and second insulated regions form substantially all of said region of overlap.

3. An electrosurgical instrument according to claim 1 wherein said first insulation regions form at least a portion of said first cutting edge and said second insulation regions form at least a portion of said second cutting edge.

4. An electrosurgical instrument according to claim 1 wherein said first cutting edge comprises said first insulation regions and said first electrode regions and said second cutting edge comprises said second insulation regions and said second electrode regions.

* * * * *